United States Patent
Shen et al.

(10) Patent No.: US 11,415,407 B2
(45) Date of Patent: *Aug. 16, 2022

(54) FREQUENCY-DOMAIN OPTICAL INTERFEROMETRY IMAGING APPARATUS AND METHOD FOR ASTIGMATISTIC BI-FOCAL ILLUMINATION IMAGING OF AN EYE

(71) Applicant: THE UNIVERSITY OF LIVERPOOL, Liverpool (GB)

(72) Inventors: Yaochun Shen, Liverpool (GB); Yalin Zheng, Liverpool (GB); Yue Dong, Liverpool (GB); Samuel Lawman, Liverpool (GB)

(73) Assignee: THE UNIVERSITY OF LIVERPOOL, Liverpool (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/036,295

(22) Filed: Sep. 29, 2020

(65) Prior Publication Data

US 2021/0010795 A1  Jan. 14, 2021

Related U.S. Application Data

(63) Continuation of application No. 16/090,409, filed as application No. PCT/GB2017/050934 on Apr. 3, 2017, now Pat. No. 10,788,309.

(30) Foreign Application Priority Data

Apr. 1, 2016 (GB) ..................... 1605616

(51) Int. Cl.
*G01B 9/02* (2022.01)
*G01B 9/02056* (2022.01)
(Continued)

(52) U.S. Cl.
CPC .......... *G01B 9/02057* (2013.01); *A61B 3/102* (2013.01); *A61B 3/12* (2013.01);
(Continued)

(58) Field of Classification Search
CPC ............ G01B 9/02057; G01B 9/02037; G01B 9/02044; A61B 3/14; A61B 3/12; A61B 3/102
See application file for complete search history.

(56) References Cited

U.S. PATENT DOCUMENTS

| 5,321,501 A | 6/1994 | Swanson et al. |
| 6,084,672 A | 7/2000 | Lewin |

(Continued)

FOREIGN PATENT DOCUMENTS

| AT | 507140 A2 | 2/2010 |
| CN | 201055372 Y | 5/2008 |

(Continued)

OTHER PUBLICATIONS

Summons to Attend Oral Proceedings in corresponding Euorpean Patent Application No. 17716008.2 dated Feb. 23, 2021.
(Continued)

*Primary Examiner* — Hwa Andrew Lee
(74) *Attorney, Agent, or Firm* — Lando & Anastasi, LLP (57) ABSTRACT

Embodiments of the present invention provide a method and apparatus for frequency-domain optical interferometry imaging. Embodiments of the invention include an apparatus comprising a line-shaping optical element for directing optical radiation into a line illumination, an imaging optical element for receiving optical radiation comprising radiation reflected from a target sample and a reference point associated with the target sample, and a detection unit for measuring common path interferences between a plurality of reflections from the target sample and the reference point.

(Continued)

Embodiments of the invention include a method comprising directing radiation into a line illumination, directing the line illumination towards a target sample, receiving radiation reflected from the target sample at a detection unit, and measuring common path interferences between a plurality of reflections at the target sample and a reference point.

31 Claims, 9 Drawing Sheets

(51) Int. Cl.
  *A61B 3/12* (2006.01)
  *A61B 3/10* (2006.01)
  *A61B 3/14* (2006.01)
(52) U.S. Cl.
  CPC ............ *A61B 3/14* (2013.01); *G01B 9/02037* (2013.01); *G01B 9/02044* (2013.01)

(56) References Cited

U.S. PATENT DOCUMENTS

| | | | |
|---|---|---|---|
| 6,208,415 | B1 | 3/2001 | De Boer et al. |
| 6,927,860 | B2 | 8/2005 | Podoleanu et al. |
| 7,072,045 | B2 | 7/2006 | Chen et al. |
| 7,330,273 | B2 | 2/2008 | Podoleanu et al. |
| 7,355,716 | B2 | 4/2008 | de Boer et al. |
| 7,463,364 | B2 | 12/2008 | Yacoubian |
| 7,648,242 | B2 | 1/2010 | Ferguson et al. |
| 7,821,647 | B2 | 10/2010 | LeBlanc et al. |
| 7,859,679 | B2 | 12/2010 | Bouma et al. |
| 7,999,935 | B2 | 8/2011 | Dyba |
| 8,174,704 | B2 | 5/2012 | Kim |
| 8,280,131 | B2 | 10/2012 | Kempe et al. |
| 8,422,023 | B2 | 4/2013 | Podoleanu |
| 8,773,760 | B2 | 7/2014 | Gmitro et al. |
| 8,797,551 | B2 | 8/2014 | Kulkarni et al. |
| 8,934,104 | B2 | 1/2015 | Koerner et al. |
| 9,304,191 | B2 | 4/2016 | Nagae et al. |
| 9,332,902 | B2 | 5/2016 | Tumlinson et al. |
| 9,615,735 | B2 | 4/2017 | Huang et al. |
| 9,816,803 | B2 | 11/2017 | Kulkarni |
| 10,024,650 | B2 | 7/2018 | Arieli et al. |
| 2008/0123103 | A1* | 5/2008 | Fujii .................. G01B 11/2441 356/496 |
| 2010/0208270 | A1 | 8/2010 | Kulkarni et al. |
| 2010/0245836 | A1 | 9/2010 | Kulkarni et al. |
| 2011/0001988 | A1* | 1/2011 | Pahk .................. G01B 11/0625 356/630 |
| 2011/0228279 | A1 | 9/2011 | Lucey |
| 2011/0261367 | A1 | 10/2011 | Gmitro et al. |
| 2012/0147326 | A1 | 6/2012 | Yatagai et al. |
| 2012/0194661 | A1 | 8/2012 | Lee et al. |
| 2014/0028974 | A1 | 1/2014 | Tumlinson |
| 2014/0125952 | A1 | 5/2014 | Buckland et al. |
| 2014/0180075 | A1 | 6/2014 | Kulkarni |
| 2015/0168250 | A1 | 6/2015 | Saxer et al. |
| 2015/0216407 | A1 | 8/2015 | Huang et al. |
| 2015/0233700 | A1 | 8/2015 | Schmoll et al. |
| 2015/0292860 | A1 | 10/2015 | Podoleanu et al. |
| 2016/0102970 | A1* | 4/2016 | Jo ..................... G01B 9/02034 356/451 |
| 2016/0206193 | A1 | 7/2016 | Schmoll et al. |
| 2017/0188815 | A1 | 7/2017 | Huang et al. |
| 2018/0156597 | A1* | 6/2018 | Smith ................ G01B 9/02035 |

FOREIGN PATENT DOCUMENTS

| | | | |
|---|---|---|---|
| EP | 0963540 | A1 | 12/1999 |
| EP | 1870029 | A1 | 12/2007 |
| EP | 1887926 | B1 | 7/2014 |
| EP | 2942619 | A1 | 11/2015 |
| WO | 9518951 | A1 | 7/1995 |
| WO | 2014137290 | A1 | 9/2014 |
| WO | 2015052071 | A1 | 4/2015 |
| WO | 2015154313 | A1 | 10/2015 |
| WO | 15189174 | A2 | 12/2015 |
| WO | 2016024270 | A2 | 2/2016 |

OTHER PUBLICATIONS

International Search Report and Written Opinion from International Application No. PCT/GB2017/050934 dated Jun. 9, 2017.
Search Report from United Kingdom Application No. GB1605616.0 dated Aug. 19, 2016.
Yaqoob et al., "Improved phase sensitivity in spectral domain phase microscopy using line-field illumination and self phase-referencing". Optics Express, vol. 17, No. 13 (2009), pp. 10681-10687.
Harasaki et al. "Improved vertical-scanning interferometry", Applied Optics (2000) vol. 39, No. 13, pp. 2107-2115.
Huang et al. "Optical Coherence Tomography", Science (1991), vol. 254, No. 5035, pp. 1178-1181.
Fercher et al. "Measurement of intraocular distances by backscattering spectral interferometry", Optics Communications (1995) vol. 117, pp. 43-48.
Grajciar et al. "Parallel Fourier domain optical coherence tomography for in vivo measurement of the human eye", Optics Express (2005) vol. 13, No. 4, pp. 1131-1137.
International Preliminary Report on Patentability in Application No. PCT/GB2017/050934 dated Oct. 2, 2018.

* cited by examiner

A: Raw OCR Image of a clear coating on metalic paint layer — 610

B: Image of Reference Signal — 620

A with normalised(B) subtracted — 630

FREQUENCY-DOMAIN OPTICAL INTERFEROMETRY IMAGING APPARATUS AND METHOD FOR ASTIGMATISTIC BI-FOCAL ILLUMINATION IMAGING OF AN EYE

CROSS-REFERENCE TO RELATED APPLICATIONS

This application claims priority under 35 U.S.C. § 120 as a continuation of U.S. patent application Ser. No. 16/090,409, titled "FREQUENCY-DOMAIN OPTICAL INTERFEROMETRY IMAGING APPARATUS AND METHOD FOR ASTIGMATISTIC BI-FOCAL ILLUMINATION IMAGING OF AN EYE," filed Oct. 1, 2018, which is a U.S. National Stage Application under 35 U.S.C. § 371 of International PCT Application No. PCT/GB2017/050934 titled "OPTICAL INTERFEROMETRY APPARATUS AND METHOD," filed Apr. 3, 2017, which claims priority to United Kingdom Application No. 1605616.0, filed Apr. 1, 2016, each of which is incorporated by reference herein in its entirety.

The present invention relates generally to the field of optical interferometry. The present invention is applicable, but not exclusively, to the imaging of complex coating structures and biological tissues such as that of the eye.

BACKGROUND

Optical interferometry is a technique in which the interference properties of light are used to obtain high resolution images and/or measure properties in a diversity of materials.

Examples of techniques which use the interferometry method include optical coherence tomography (OCT) and optical coherence reflectometry (OCR). OCT is a non-invasive imaging technique that can uses light to produce sub-surface, cross-sectional images from within optical scattering media. OCR is a similar measurement technique that processes the interference patterns of reflected waves from a sample to determine sample structural characteristics. Due to its ability to achieve micrometre resolution, the clinical adoption of OCT in ophthalmology in particular is now well established and commercial systems are in routine use for research and clinical applications.

It is desired to improve upon one or more of scanning speeds, achieved displacement or motion sensitivity, and resolution of interferometry systems.

It is an object of embodiments of the invention to at least mitigate one or more of the problems of the prior art.

BRIEF DESCRIPTION OF DRAWINGS

One or more embodiments of the invention will now be described, by way of example only, with reference to the accompanying figures, in which.

DETAILED DESCRIPTION OF EMBODIMENTS OF THE INVENTION

Figure 1A:
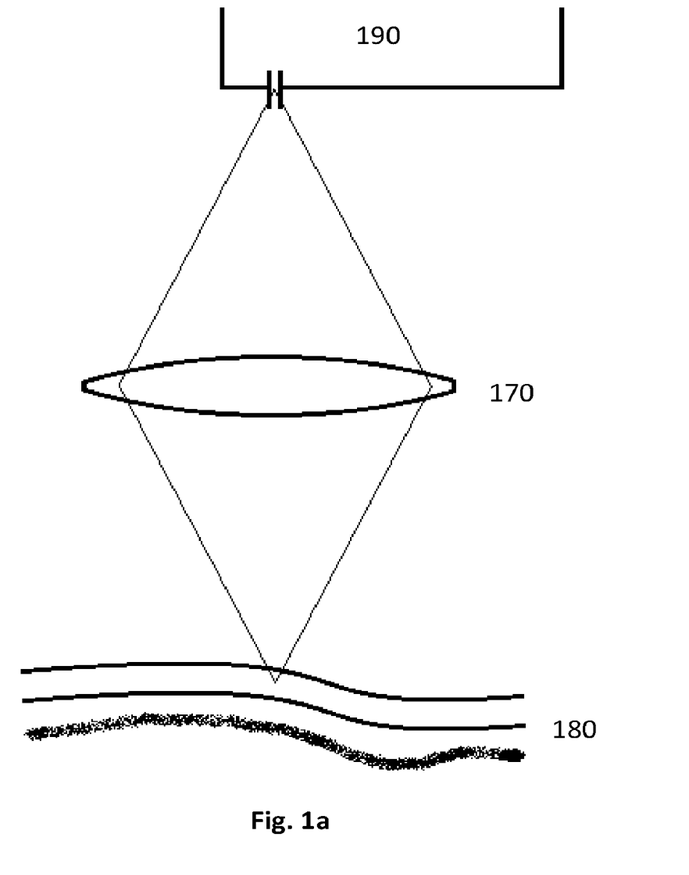
FIG. 1a shows an OCT or OCR system in accordance with an embodiment of the present invention.

FIG. 1a shows a common-path line-field OCT system according to an embodiment of the present invention. The system in FIG. 1a comprises an imaging lens or lens system 170, a target sample 180, and a detection unit 190. The detection unit 190 may be arranged to measure common path interferences between a plurality of reflections from the target sample 180 and at least one reference point. In some embodiments, the imaging lens 170 may be a spherical or aspherical refractive or reflective lens or lens system i.e. comprising more than one lens. In some embodiments, the detection unit 190 may be a spectrograph. The detection unit 190 may comprise a line-imaging spectrograph system. The spectrograph 190 may be arranged to produce spectres spatially resolved in one lateral dimension. In some embodiments, the target sample 180 may be illuminated by an external source of optical radiation. The optical radiation may be a line illumination. The target sample 180 may be arranged relative to the imaging lens 170 such that optical radiation reflected from the target sample 180 is directed by the imaging lens 170 towards the detection unit 190. Depending on various characteristics of the target sample 180, after being directed by the at least one imaging lens 170 the radiation is reflected or scattered back from at least two points on the surface of, within, or external to the target sample 180. The points of reflection comprise at least one reference point and one sample point. As will be explained later, the interference pattern given by the combination of the reflected wave fronts from at least these two points provides information on the characteristics of the target sample 180, and is thus measured at the detection unit 190.

Figure 1B:
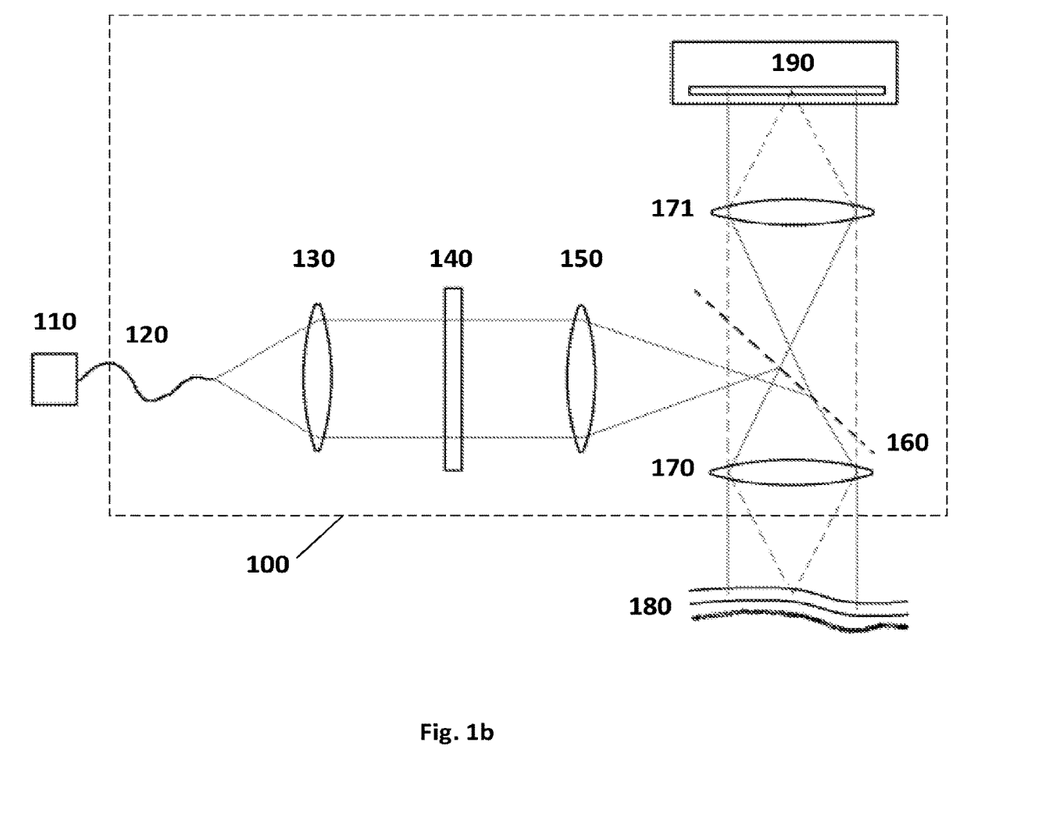
FIG. 1b shows an OCT or OCR system in accordance with an embodiment of the present invention.

FIG. 1b illustrates a common-path line-field OCT system 100, in accordance with another embodiment of the present invention. The system 100 comprises a line-shaping optical element for directing light into a line-field focus 150, the imaging lens element 170, and the detection unit 190 as previously described unless stated otherwise. The system 100 also optionally comprises a wave guide 120, a collimator lens 130, and an optical filter 140. In some embodiments, there may exist a further imaging element 171. In some embodiments, the line-shaping optical element 150 may be a line-field gate element that is instead incorporated into imaging optical elements. In some embodiments there may further exist a beam splitting means 160. In some embodiments, the detection unit 190 may include one or more processing means, such as one or more processing devices, arranged to perform further processing on the images received by the detection unit 190. Included in FIG. 1b is also a source of optical radiation 110 and the target sample 180. In some embodiments, the system 100 is arranged such that illumination provided by the source of optical radiation 110 is first directed via the wave guide 120 towards the collimator lens 130. However, it should be realised that the wave guide 120 and collimator lens 130 may be absent in some cases, for example if the source of illumination is provided by a suitable light source. A suitable light source may be one which provides directed or collimated light such as a light emitting device which may be, for example, one or more LEDs.

In some embodiments, the optical radiation 110 may comprise low-coherence light, or broadband EM radiation within one or more of a visible, infra-red, and/or ultraviolet spectrums. In some embodiments, the optical radiation 110 may be provided by multiple sources of optical radiation. In some embodiments, the optical radiation 110 may comprise radiation provided by multiple sources of optical radiation combined together. For example, the optical radiation 110 may comprise combined radiation beams each having a differing phase or optical path length. In some embodiments, the optical radiation 110 may comprise multiple radiation beams provided by a single source of optical radiation, wherein each beam has a differing phase or optical path length, and the multiple radiation beams are split from the single source of optical radiation via a beam splitter or by any other suitable method. In some embodiments, the wave guide 120 may comprise an optical fibre 120.

After passing through the collimator lens 130, collimated radiation is then passed through the filter 140. The filter 140 is arranged to control spectral intensities of the radiation passing therethrough. In some embodiments, the filter 140 is bandpass in nature and only permits wavelengths between first and second wavelengths such as 700-1000 nm to pass through. In some embodiments, multiple filters may be used in combination.

In some embodiments, radiation having exited the filter 140 is then directed towards the line-shaping optical element 150. In some embodiments, the line-shaping optical element 150 may be a cylindrical or a cylindrical lens. In other embodiments, the line-shaping optical element 150 may be a line-field gate. In some embodiments, the line-shaping optical element 150 may be incorporated into the entrance of the detection unit 190. Shaping the radiation into a line illumination via the line-shaping optical element 150 allows the exposure time to be significantly reduced when imaging, which may result in one or more of quicker B-scan speeds, reduced distortion, and fewer image artefacts. Motion artefacts in particular can be reduced using the line-field focus. In addition, the line-field focus gives two spatial dimensions when imaging without the need for moving parts, thus simplifying the overall imaging mechanism. Finally, phase information may also be preserved using this method of imaging. Preserving phase information allows for improved sensitivity of measurement, wherein the sensitivity refers to either changes in optical displacement, such as thickness of the target sample with time, the difference in thickness between laterally adjacent points, difference in height in laterally adjacent points (i.e. profilometry) or change in material refractive index spatially or temporally.

In some embodiments, the line illumination is then directed towards the target sample 180 via the imaging lens element 170. In some embodiments, the imaging lens 170 may be a spherical or aspherical refractive or reflective lens or lens system. Depending on various characteristics of the target sample 180, after being directed by the imaging lens element 170 the radiation is reflected or scattered back from at least two points on the surface of, within, or external to the target sample 180. The points of reflection comprise at least one reference point and one sample point. The interference pattern given by the combination of the reflected wave fronts from these two points provides information on the characteristics of the target sample, and is thus measured at the detection unit 190.

In other embodiments, the setup may include the use of a beam splitting means 160 to allow the same path to be used for illumination and imaging. Use of a beam splitting means 160 also allows the apparatus to be adapted for conventional interferometry situations. The beam-splitting means 160 directs at least a portion of the illuminating radiation towards the imaging lens element 170 and the target sample 180, and at least a portion of the reflected radiation reflected from at least two points on the surface of, within, or external to the target sample 180 is returned to the detection unit 190 via the same beam splitting means 160 along the same path. In some embodiments, the imaging lens element 170 may be a spherical or aspherical refractive or reflective lens or lens system. The imaging lens element 170 is arranged to produce an image of the target sample 180 at the detection unit 190.

In some embodiments, at least one reference point consists of an area external to the target sample 180, for example a reference mirror or a coverslip adjacent to the target sample. In other embodiments, at least one reference point comprises an area positioned within the target sample 180. In still other embodiments, at least one reference point is an area on the surface of the target sample 180.

In some examples, the at least one reference point is an area on the imaging lens element 170 itself, i.e. via a Mirau setup.

In still further embodiments, the interference image is given at least partially by the superposition of multiple effective reflected reference signals, taken from multiple effective reference points. For example, in applications where the target comprises a human eye the reference points may, for example, correspond to the surface of the tear film, interface, or other reflecting or scattering component of an applied contact lens or other artificial body, or any other appropriate or taken reflection/scatterer within or associated with the eye. In embodiments where the source of optical radiation 110 comprises multiple sources, the multiple reference points may correspond to multiple sources of optical radiation. The multiple reference points may be taken from at least one of on the surface, within, or external to the target sample.

Arranging at least some of the reference points to be adjacent or part of the sample allows for a much greater tolerance on the axial positioning of the target sample when compared with prior art OCT implementations, and also gives increased stability of interference as movements of the target sample 180 during the imaging process are compensated by the equivalent positional shift of the reference point. This reduces the likelihood of motion artefacts in the final image.

In some embodiments, the further imaging element 171 may be a further imaging lens element 171 which may be arranged in relation to the first imaging lens element 170 to receive the reflected beams and to produce an image of the target sample 180 at the detection unit 190. In some embodiments, the further imaging lens element 171 may be a spherical or aspherical refractive or reflective lens or lens system.

In some embodiments, the positions of the optical elements 150 and 170 are moveably mounted such that the arrangement of focal distances of the optical elements 150 and 170 can be varied. This allows for a method of astigmatistic bi-focal illumination of the target sample 180, which will be explained later.

In some embodiments, the detection unit 190 receives a combination of the image and the reference beams, and measures the resulting common-path interference. These interferences are further measured between a plurality of reflections at the target sample 180 and the reference point. These measurements are used to produce tomographic images.

In some embodiments, the detection unit 190 may comprise a spectrograph. In some embodiments, the detection unit 190 may be equipped with a 2D detection unit array, where each array element outputs a respective value or signal, such as a CCD or CMOS/sCMOS array. In some embodiments, the detection unit 190 may comprise processing means for processing the received images. At the detection unit 190, an array of spectra is obtained from the raw image data received from the reflected and back-scattered radiation from the target sample 180. In some embodiments, the array of spectra is obtained with a uniform wavenumber (frequency) spacing.

In other embodiments, if the spectra are not already in uniform wavenumber spacing, they may be mathematically interpolated via the processing means into equal wavenumber spacing. An apodisation or digital spectrum shaping method may be applied to reduce one or more of any axial point spread function artefacts/side lobes and/or manipulate the axial point spread function shape.

A generic Discrete Fourier Transform (DFT) algorithm can then be applied to each spectra via processing means, thus retrieving the complex A-scan. Multiple A-scans can thus be combined to give a B-scan, comprising a two-dimensional, cross-sectional view of areas within the target sample.

In some embodiments, a normalised reference signal taken from a single interface measurement is subtracted from the measurements in order to reduce any DC components or static artefacts in the images.

In some embodiments, the thickness of a layer can be found by taking the peak magnitude points within the A-scan and finding the (approximate) centre of the axial point spread function via the processing means, thus allowing recovery of the position of the interface. In other embodiments, layer thicknesses can also be extracted using the B-scan map via image segmentation.

In an embodiment of the present invention, the thickness of the layer can also be found via the processing means using phase information that is preserved as a result of using a line illumination. In this method, the relative differences in the thicknesses of a layer temporally and/or spatially can be obtained from the complex phase of the interference data. The highest value magnitude pixels are first selected from the received images at the detection unit 190, and their phases are extracted for use. In some embodiments, the selected pixels may simply be pixels with a signal-to-noise-ratio (SNR) value above a predetermined threshold. Phase difference constants between pixels of different depths may be corrected by adding or subtracting an appropriate value and phase un-wrapping techniques may further be applied to obtain a continuous phase map.

This multi-dimensional data may then be multiplied by $\lambda/4\pi$, where $\lambda$ is the appropriate effective central wavelength of light. The result is the relative thickness differences of each layer in the target sample.

In some embodiments, conversion to absolute thickness can be achieved by subtracting the average value and adding an average thickness calculated by any methods that return the (approximate) centre of the axial point spread function.

Using phase information to calculate layer thicknesses allows for higher precision than obtaining it from axial point spread functions.

Figure 2:
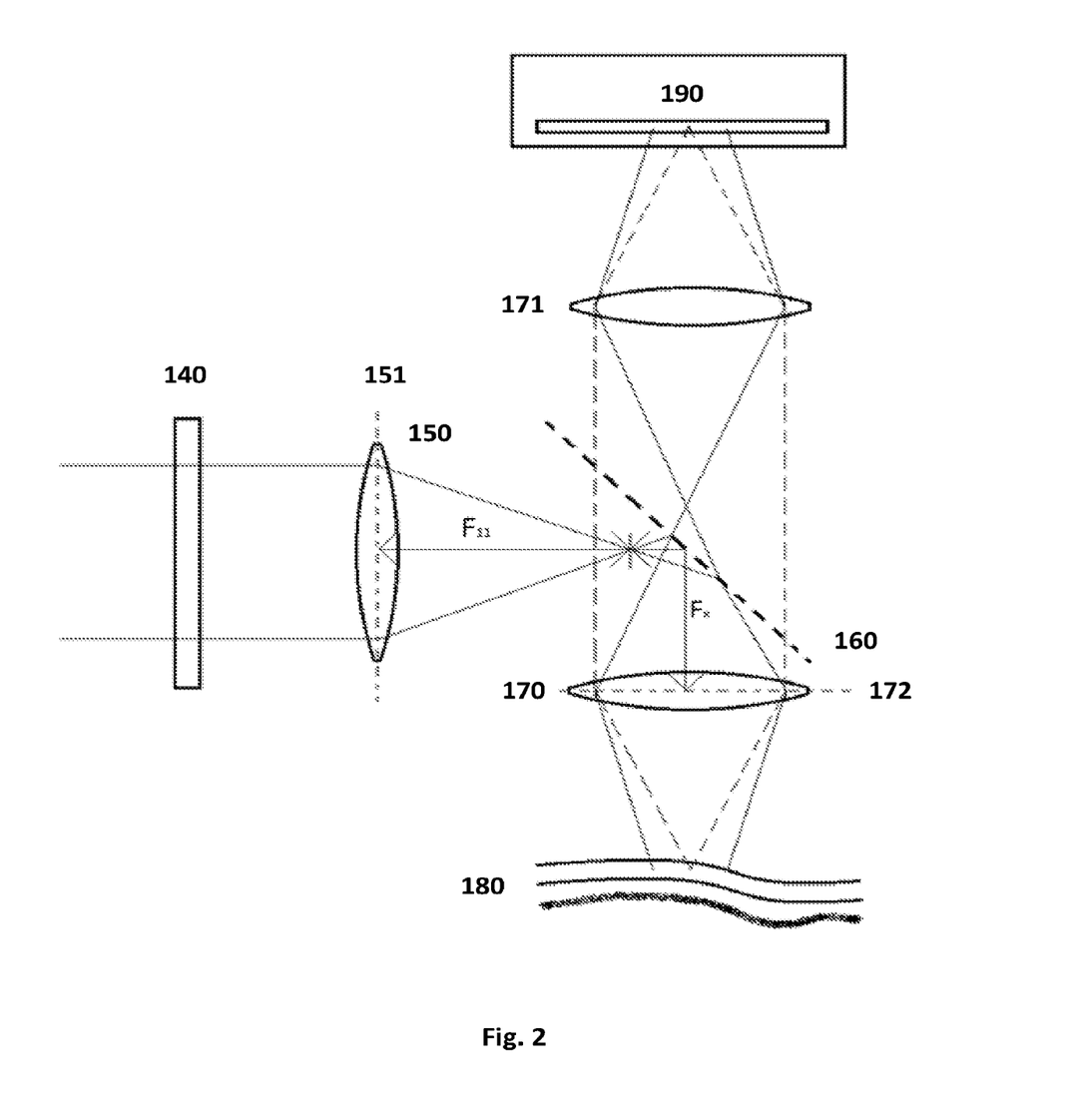
FIG. 2 shows an OCT or OCR system in accordance with another embodiment of the present invention.

FIG. 2 shows a common-path line-field OCT system 200, with the astigmatistic bi-focal illumination setup shown in more detail, in accordance with an embodiment of the present invention.

In one embodiment of the present invention, flat, collimated wave fronts of illuminating radiation are used for imaging the target sample 180. However this method can present certain issues depending on the nature of the target sample 180. Taking imaging in the cornea as an example, using flat, collimated wave fronts may cause the light to be focused by the eye onto the retina, increasing incident light intensity on the retina and posing potential health hazards to the patient.

Astigmatistic bi-focal illumination mitigates this problem by bringing the radiation to a focus at a different point than the retina (such as that corresponding with the centre of the curvature of the cornea). This decreases the incident light intensity at the retina and any health and safety limitations become near identical to that of single point scanning OCT systems. As shown in 200, this can be achieved by varying the positions of the line-shaping optical element 150 and/or the imaging lens element 170.

Positioning the line-shaping optical element 150 at position 151 gives a line-shaping optical element focal distance of $F_{cyl}$. Similarly, positioning the imaging lens element 170 at position 172 gives an imaging lens element focal distance of $F_{obj}$. In one embodiment, astigmatistic bi-focal illumination is achieved by arranging the position of optical elements 150 and 170 such that:

$$F_x = \frac{1}{\frac{1}{F_{obj}} - \frac{1}{F_{obj} + \Delta F}}$$

where $\Delta F$ is the difference in depth between the two illumination focal points in the two lateral dimensions perpendicular to the direction of travel of light, caused by the interaction of the line-shaping optical element 150 and other illuminating lenses e.g. the imaging lens element 170. The astigmatistic nature of the line-shaping optical element 150 causes light propagating in the two perpendicular planes to have different focal points. When optimised in conjunction with the imaging lens 170, these two focal points form $F_{Obj}$ and $F_{Obj}+\Delta F$ respectively. $F_x$ is the difference in distance between the focal point of the line-shaping optical element 150 and the imaging lens 170 itself.

Figure 3:
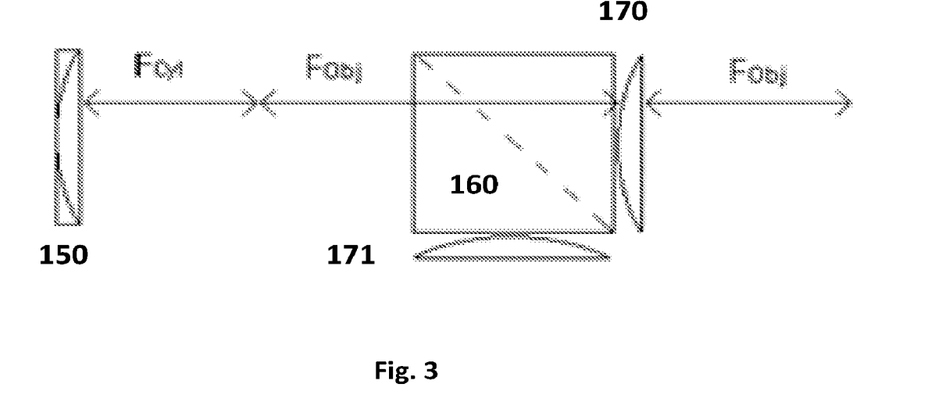
FIG. 3 shows a schematic of an embodiment of the present invention.

FIG. 3 shows an arrangement of the line-shaping optical element 150 and the imaging lens 170 without a bi-focal astigmatistic illumination set-up. It can be see that $F_{cyl}$ is the focal distance of the line-shaping optical element 150 and $F_{obj}$ is the focal distance of the imaging lens 170. In this embodiment, $F_x$ is the same as $F_{obj}$.

Figure 4:
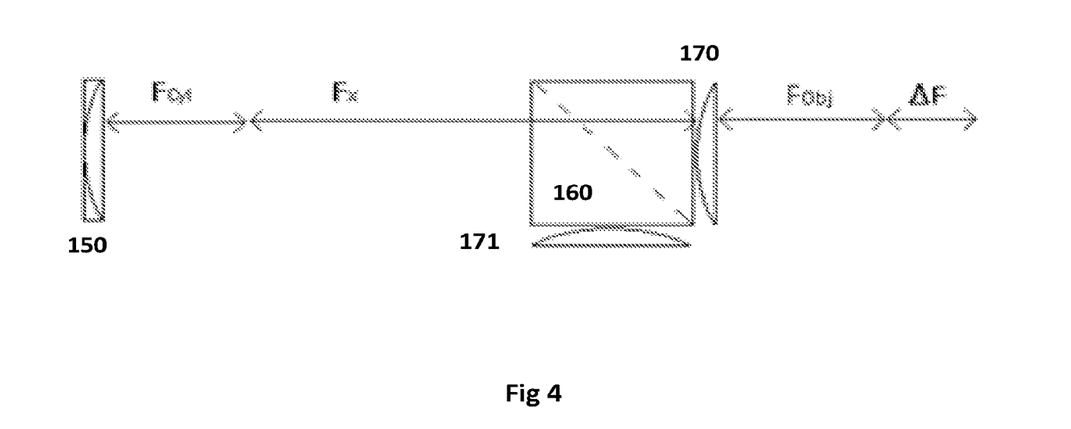
FIG. 4 shows a schematic of another embodiment of the present invention.

FIG. 4 shows an arrangement of the line-shaping optical element 150 and the imaging lens 170 with a bi-focal astigmatistic illumination set-up. In this arrangement, the line-shaping optical element 150 is positioned such that the distance between the line-shaping optical element focal point 150 and the imaging lens 170 is given by $F_x$. Furthermore, the astigmatistic nature of the line-shaping optical element 150 brings rise to $\Delta F$, as explained above.

Figure 5:
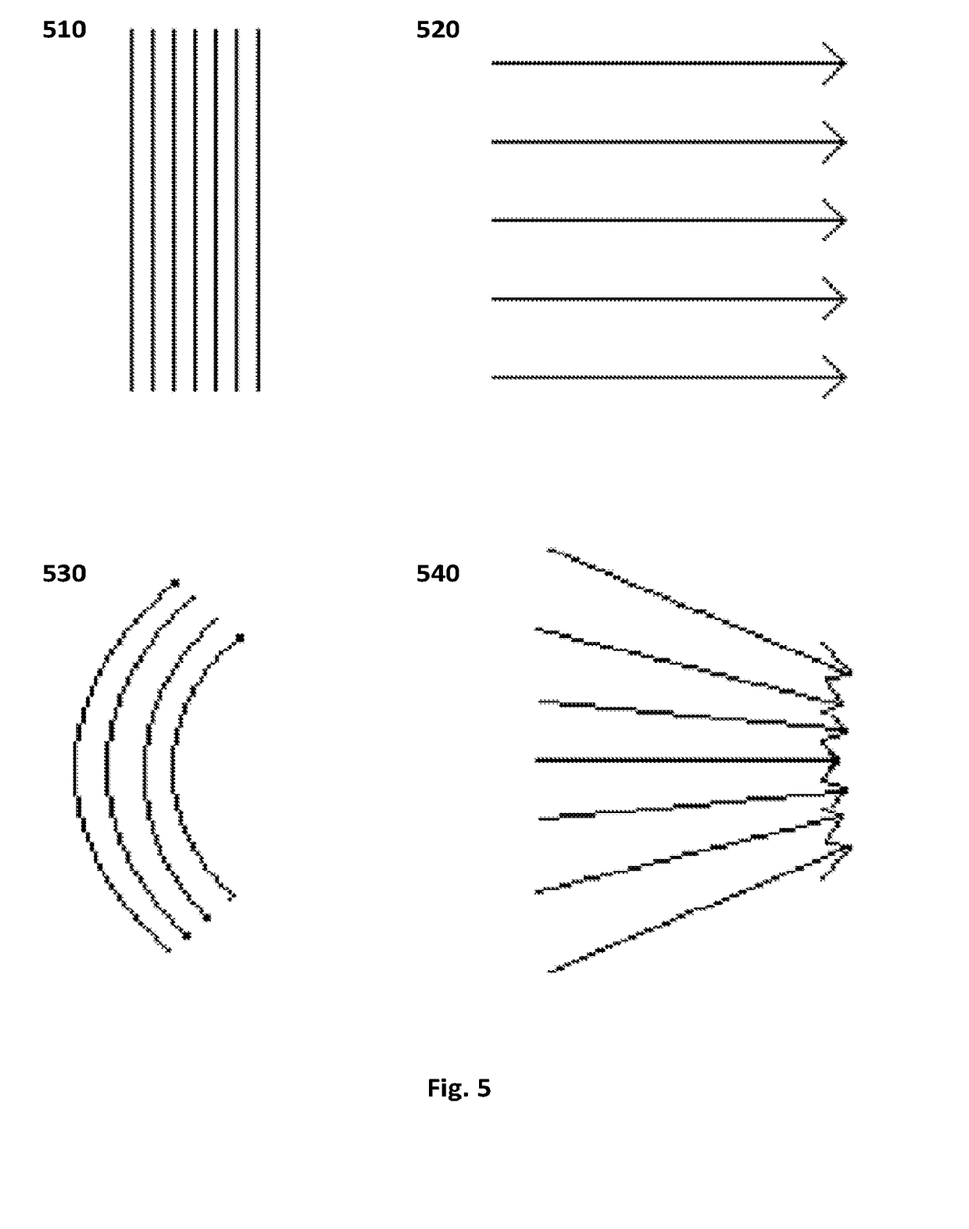
FIG. 5 shows a schematic illustration according to an embodiment of the present invention.

FIG. 5 shows the wave fronts of illuminating light at the focus of a common-path line-field OCT system for conventional and astigmatistic bi-focal line-field OCT, in accordance with one embodiment of the present invention. 510 shows collimated light wave fronts as in conventional systems, and 520 shows the equivalent ray tracing representation. 530 shows the light wave fronts when astigmatistic bi-focal illumination is implemented, and similarly 540 shows the equivalent ray tracing representation.

It will be appreciated by the skilled person that applications of the invention are not limited to biological imaging. As well as biological uses, applications of embodiments of the invention include the measurement of coating thicknesses, such as in industrial applications i.e. manufacturing, quality control etc. For example, non-opaque coatings are used to provide protection and aesthetic enhancement to a wide variety of objects—examples include heavy industry clear top coats in modern car paint systems, varnishing on outdoor wooden objects, and the highly specialised varnish coatings for valuable works of art. Precise and accurate measurement of the thickness of these coatings are then useful for quality assurance purposes in particular. It will be appreciated that the usefulness of embodiments of the invention are not limited to these coatings.

Figure 6:
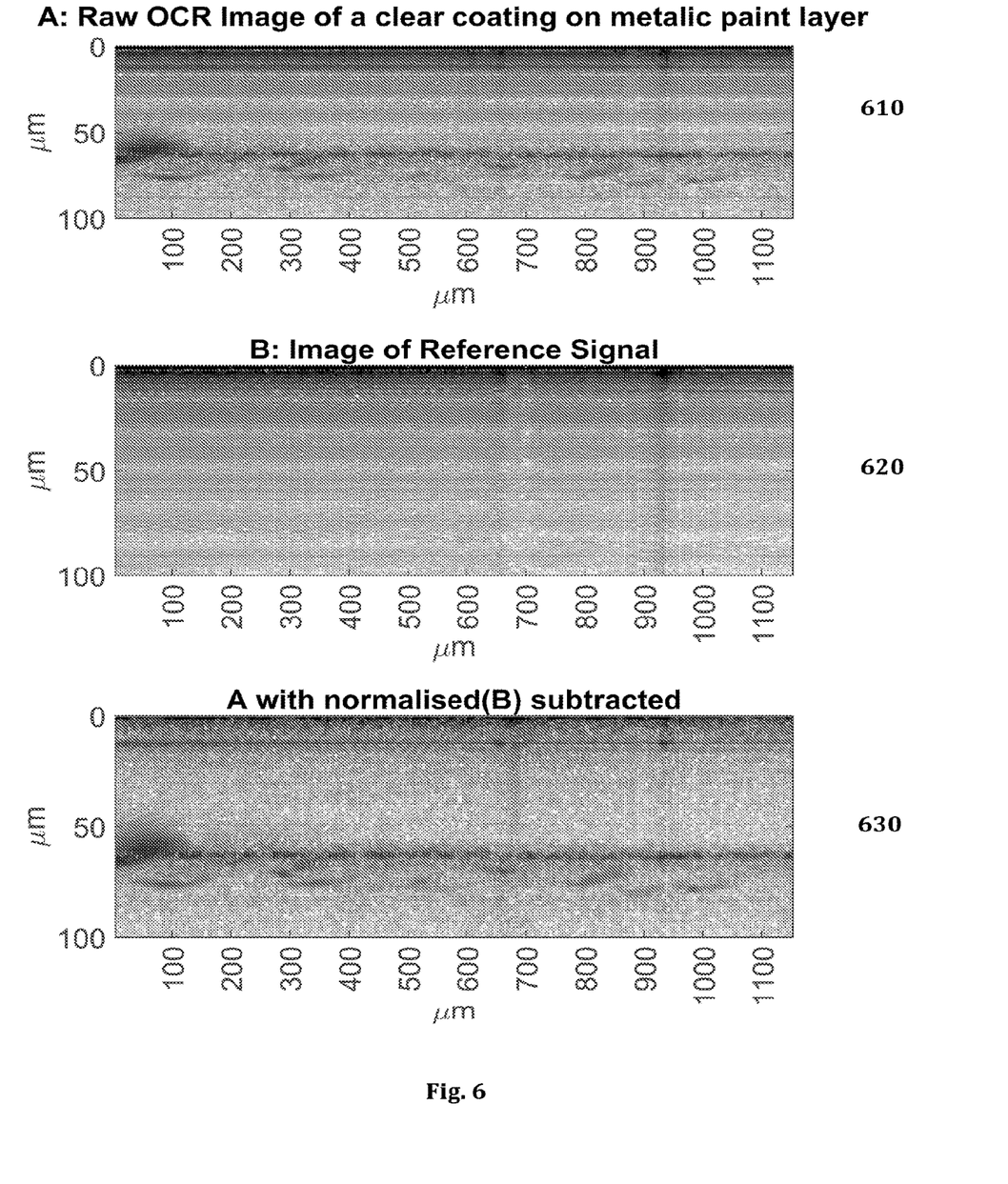
FIG. 6 shows an example image produced according to an embodiment of the present invention.

FIG. 6 shows an example OCT image produced according to an embodiment of the invention. The target sample imaged in this instance is a multilayer automotive paint panel. The reference points associated with the target sample comprised of the surface of a top (uppermost) paint layer only, giving a clear OCT image of the layered structure underneath the top paint layer. 610 shows an image indicative of the spectral data measured according to an embodiment of the invention, with post-processing applied. The post-processing applied in this example comprised interpolation, Fourier Transform, and logging of the measured spectral data, however it will be appreciated that other post-processing techniques may be applied. 620 shows a reference of a single reflecting surface. 630 shows an enhanced version of 610, created by subtracting 620 from 610. With such images, it will be realised that processing or analytical methods applicable to conventional OCT systems may be applied to the invention.

Figure 7:
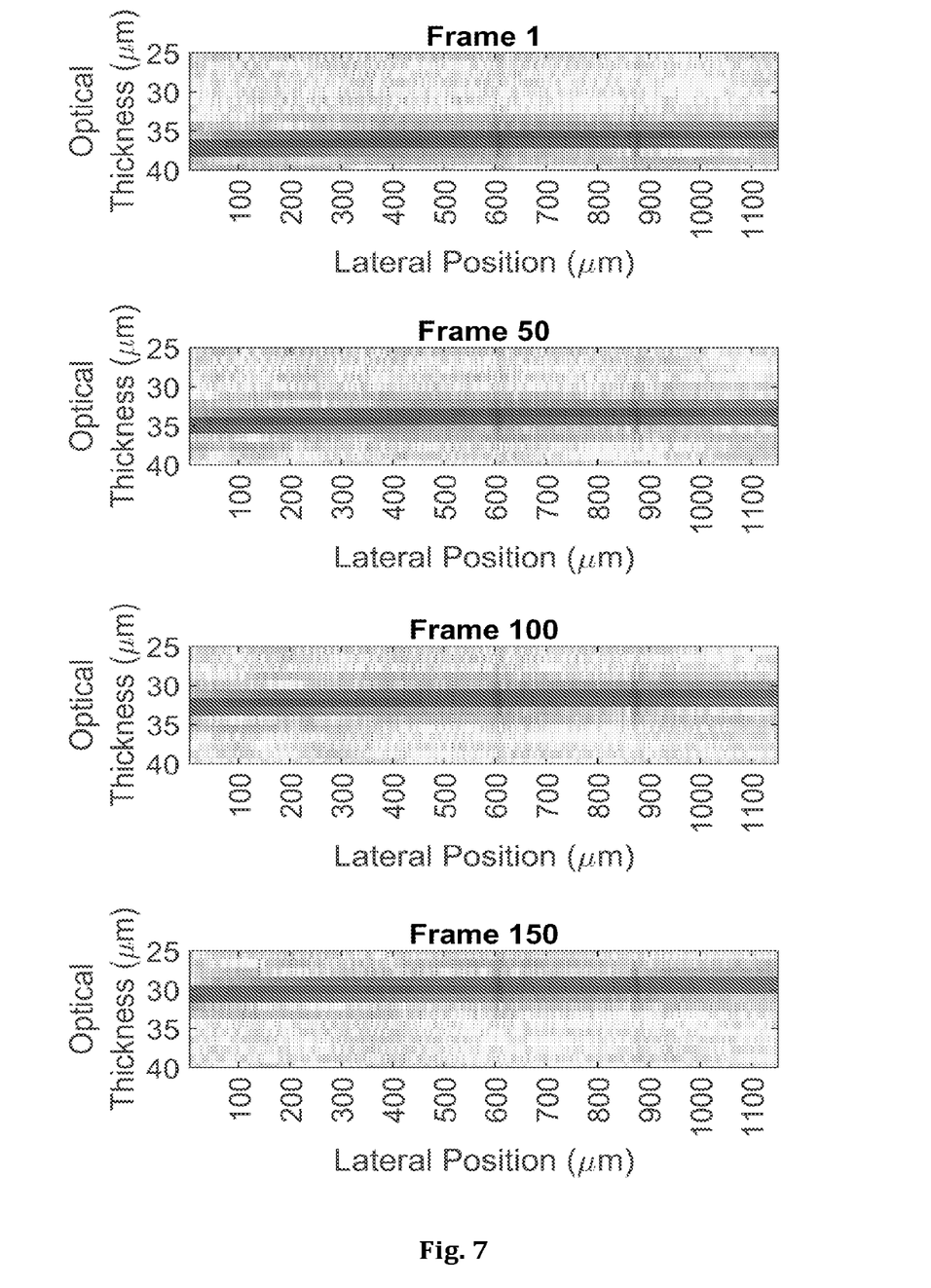
FIG. 7 shows an example image produced according to an embodiment of the present invention.

FIG. 7 shows an example OCT image produced according to an embodiment of the invention. The target sample in this instance comprised a glass-varnish interface. The reference point associated with the target sample comprised a surface of the varnish. The images shown in FIG. 7 were taken at different times as the solvent varnish dried and thinned.

Figure 8:
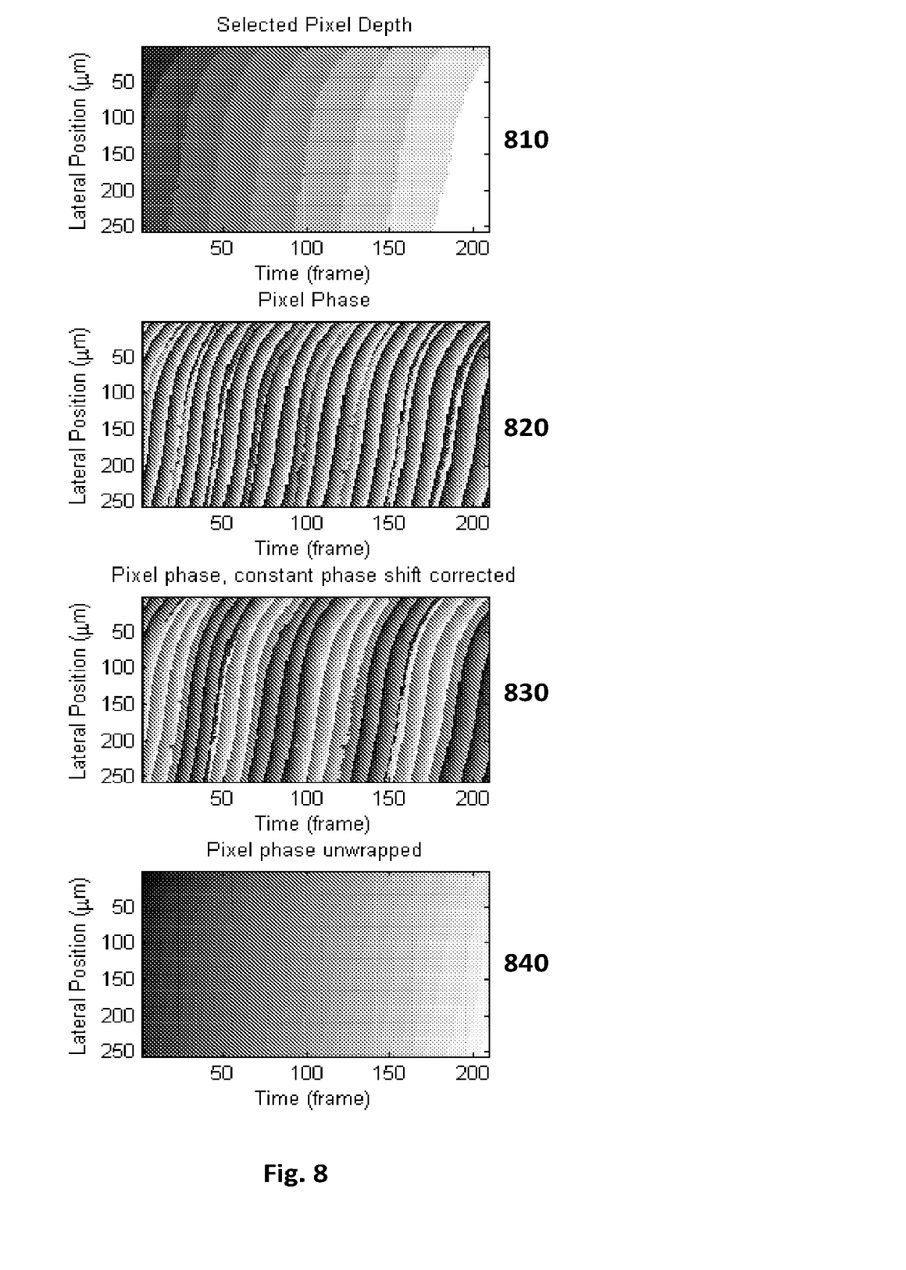
FIG. 8 shows an example image produced according to an embodiment of the present invention.

FIG. 8 shows a process of utilising the Fourier phase information produced according to an embodiment of the invention to measure changes in varnish thickness (glass-varnish interface position), with spatial (i.e. between different lateral points) and temporal (i.e. over time), and drying rate. 810 shows the pixel chosen vs. space and time. 820 shows the Fourier phase of those pixels. 830 is the Fourier phase after correction for the phase differences between pixels. 840 shows the phase after unwrapping in both (spatial and temporal) dimensions.

Figure 9:
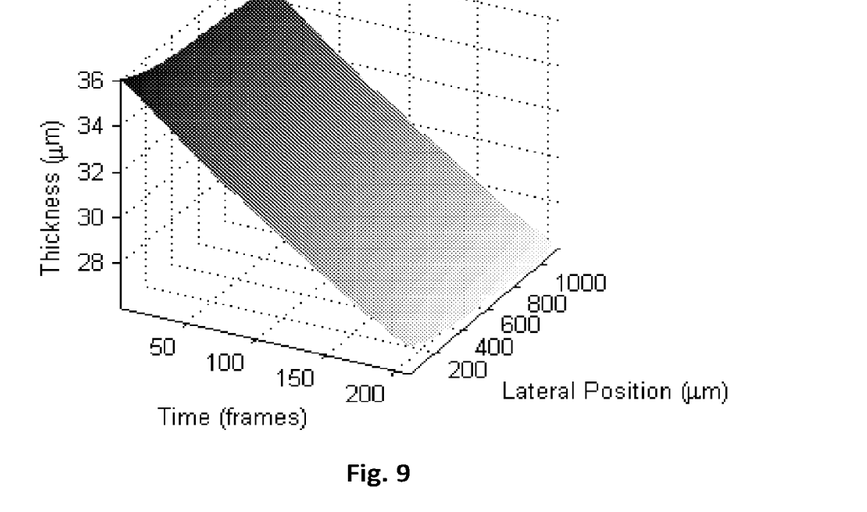
FIG. 9 shows an example image produced according to an embodiment of the present invention.

FIG. 9 shows a representation of 840 after converting from phase to thickness. Utilising Fourier phase may provide higher displacement sensitivity than using amplitude information alone.

Figure 10:
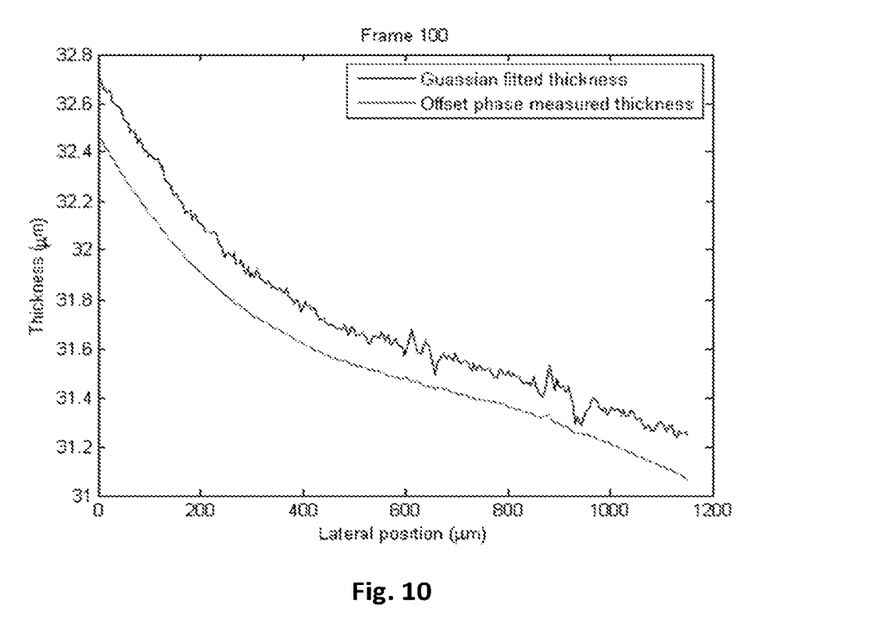
FIG. 10 shows an example image produced according to an embodiment of the present invention.

FIG. 10 shows (displaced for comparison purposes) example thickness measurements, at one position, obtained by finding the centre of the point spread function (amplitude information only) and the described Fourier phase method. FIG. 10 shows that the Fourier phase method to have lower noise.

It will be appreciated that embodiments of the present invention can be realised in the form of hardware, software or a combination of hardware and software. Any such software may be stored in the form of volatile or non-volatile storage such as, for example, a storage device like a ROM, whether erasable or rewritable or not, or in the form of memory such as, for example, RAM, memory chips, device or integrated circuits or on an optically or magnetically readable medium such as, for example, a CD, DVD, magnetic disk or magnetic tape. Such software may be tangibly stored on a computer-readable medium. The computer-readable medium may be non-stransitory. It will be appreciated that the storage devices and storage media are embodiments of machine-readable storage that are suitable for storing a program or programs that, when executed, implement embodiments of the present invention. Accordingly, embodiments provide a program comprising code for implementing a system or method as claimed in any preceding claim and a machine readable storage storing such a program. Still further, embodiments of the present invention may be conveyed electronically via any medium such as a communication signal carried over a wired or wireless connection and embodiments suitably encompass the same.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings), may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed. The claims should not be construed to cover merely the foregoing embodiments, but also any embodiments which fall within the scope of the claims.

The invention claimed is:

1. An apparatus for frequency-domain optical interferometry imaging, comprising:
   a line-shaping optical element for directing optical radiation into a line illumination;
   an imaging lens for receiving optical radiation comprising radiation reflected from a target sample and a reference point; and
   a detector for measuring interferences between a plurality of reflections from the target sample and the reference point;
   wherein the line-shaping optical element and the imaging lens are moveably mounted; and
   wherein the line-shaping optical element and the imaging lens are arranged such that $F_x$, the distance between the focal point of the line-shaping optical element and the imaging lens is $$F_x = \frac{1}{\frac{1}{F_{obj}} - \frac{1}{F_{obj} + \Delta F}}$$

where $F_{obj}$ is the focal length of the imaging lens, and $\Delta F$ is the difference in depth between two illumination focal points in two lateral dimensions perpendicular to a direction of travel of light, caused by the interaction of the line-shaping optical element and the imaging lens.

2. The apparatus of claim 1, wherein the line-shaping optical element is a cylindrical or acylindrical lens.

3. The apparatus of claim 1, further comprising a beam splitting means to direct at least a portion of the radiation.

4. The apparatus of claim 3, wherein the imaging lens is positioned between the detector and the beam splitting means.

5. The apparatus of claim 1, wherein the apparatus comprises one or more of a wave guide, a collimator lens, a beam splitting means, and/or an optical filter.

6. The apparatus of claim 1, wherein the imaging lens comprises a spherical or aspherical lens.

7. The apparatus of claim 1, wherein the imaging lens comprises a reflective or refractive lens.

8. The apparatus of claim 1, wherein the imaging lens is one of a plurality of imaging lenses.

9. The apparatus of claim 1, wherein the detector comprises a spectrograph.

10. The apparatus of claim 1, wherein the detector comprises one of a CCD, CMOS or sCMOS array.

11. The apparatus of claim 1, wherein the reference point is a point on a surface of the target sample.

12. The apparatus of claim 1, wherein the reference point is a point within the target sample.

13. The apparatus of claim 1, wherein the reference point is one of a plurality of reference points taken simultaneously.

14. The apparatus of claim 1, wherein the optical radiation is provided by multiple sources of optical radiation.

15. The apparatus of claim 1, further comprising means for moving a position of one or more of the line-shaping optical element and the imaging optical element to change a focal point of the associated optical element.

16. The apparatus as claimed in claim 1, wherein the detection unit is configured for measuring common path interferences between the plurality of reflections from the target sample and the reference point.

17. The apparatus as claimed in claim 1, wherein the reference point is associated with the target sample.

18. A method for frequency-domain optical interferometry imaging, comprising:
Directing, with a line-shaping optical element, radiation into a line illumination;
directing the line illumination towards a target sample;
receiving, via an imaging lens, radiation reflected from the target sample at a detector; and
measuring interferences between a plurality of reflections at the target sample and a reference point
wherein the line-shaping optical element and the imaging lens are moveably mounted; and
wherein the line-shaping optical element and the imaging lens are arranged such that $F_x$, the distance between the focal point of the line-shaping optical element and the imaging lens is $$F_x = \frac{1}{\frac{1}{F_{obj}} - \frac{1}{F_{obj} + \Delta F}}$$

where $F_{obj}$ is the focal length of the imaging lens, and $\Delta F$ is the difference in depth between two illumination focal points in two lateral dimensions perpendicular to a direction of travel of light, caused by the interaction of the line-shaping optical element and the imaging lens.

19. The method of claim 18, further comprising forming tomographic images from the measured interference readings.

20. The method of claim 18, comprising directing the radiation into a line illumination via a cylindrical or acylindrical lens.

21. The method of claim 18, comprising directing at least a portion of the radiation via a beam splitting means.

22. The method of claim 18, comprising further directing the radiation via a wave guide, a collimator lens, and/or an optical filter.

23. The method of claim 21, wherein the radiation is directed towards the target sample and the detector via the beam splitting means.

24. The method of claim 18, wherein the radiation is directed via a plurality of imaging lenses.

25. The method of claim 18, wherein the reference point is a point on the surface of the target sample.

26. The method of claim 18, wherein the reference point is a point within the target sample.

27. The method of claim 18, wherein the reference point is a point taken from a reflective surface external to the target sample.

28. The method of claim 18, wherein the radiation is provided by multiple sources.

29. The method of claim 18, comprising moving a position of one or more of the line-shaping optical element and the imaging lens to change a focal point of the associated optical element.

30. The method of claim 18, wherein measuring interference readings includes measuring common path interference readings between the target sample and the reference point.

31. The method of claim 18, wherein the reference point is associated with the target sample.

\* \* \* \* \*